(12) United States Patent
Cassier et al.

(10) Patent No.: US 7,534,272 B2
(45) Date of Patent: May 19, 2009

(54) AGENT FOR OXIDATIVE TREATMENT, PARTICULARLY IN TRANSPARENT GEL FORM

(75) Inventors: Thorsten Cassier, Dieburg (DE); Michael Lede, Egelsbach (DE)

(73) Assignee: Wella AG, Darmstadt (DE)

( * ) Notice: Subject to any disclaimer, the term of this patent is extended or adjusted under 35 U.S.C. 154(b) by 204 days.

(21) Appl. No.: 10/585,966

(22) PCT Filed: Jan. 7, 2005

(86) PCT No.: PCT/EP2005/000068

§ 371 (c)(1),
(2), (4) Date: Jul. 13, 2006

(87) PCT Pub. No.: WO2005/067874

PCT Pub. Date: Jul. 28, 2005

(65) Prior Publication Data

US 2007/0151044 A1 Jul. 5, 2007

(30) Foreign Application Priority Data

Jan. 16, 2004 (DE) .................. 10 2004 002 349

(51) Int. Cl.
*D06L 3/00* (2006.01)

(52) U.S. Cl. .................. 8/101; 8/107; 8/111

(58) Field of Classification Search .................. 8/101, 8/107, 111
See application file for complete search history.

(56) References Cited

U.S. PATENT DOCUMENTS

| 4,927,627 A | 5/1990 | Schrader et al. | |
| 6,540,791 B1 * | 4/2003 | Dias | 8/111 |
| 2003/0084518 A1 | 5/2003 | Schonert et al. | |
| 2004/0034944 A1 * | 2/2004 | Legrand et al. | 8/405 |

FOREIGN PATENT DOCUMENTS

| DE | 37 32 147 | 4/1989 |
| DE | 198 15 972 | 9/1999 |
| DE | 101 43 293 | 3/2003 |
| EP | 0 360 986 | 4/1990 |
| FR | 2 818 540 | 6/2002 |
| FR | 2 820 034 | 8/2002 |

* cited by examiner

*Primary Examiner*—Eisa B Elhilo
(74) *Attorney, Agent, or Firm*—Michael J. Striker

(57) ABSTRACT

A preferably clear or transparent agent in gel form for carrying out oxidative treatments in various application fields, for example cosmetics, dental technology, pharmacy and cleaning agents. The agent is particularly well suited for use in cosmetic hair treatments such as, for example, blonding, oxidative hair coloring, and permanent hair deformation. The agent contains a mixture of an oxidant, at least one peroxide stabilizer, at least one specific polymer thickener and water or an aqueous solvent.

19 Claims, No Drawings

AGENT FOR OXIDATIVE TREATMENT, PARTICULARLY IN TRANSPARENT GEL FORM

CROSS-REFEERENCE TO REALTED APPLICATIONS

This application claims priority under 35 U.S.C 119(a)-(d) to German patent application number 10 2004 002 349.2, filed 01/16/2004.

BACKGROUND OF THE INVENTION

1. Field of the Invention

The present invention relates to a, preferably clear or transparent, agent in gel form for carrying out oxidative treatments in various application fields, such as, for example, cosmetics, dental technology, pharmacy and cleaning agents. is particularly well suited for use in cosmetic hair treatments, for example blonding, oxidative hair dyeing and the fixation of permanently deformed hair. The agent of the invention contains a mixture of an oxidant, at least one stabilizer, at least one specific polymer thickener and water or an aqueous solvent.

The need for such an agent will be illustrated in the following using the hair cosmetics field as an example. In the hair cosmetics field, oxidant-containing hair-treatment agents are used for various applications, hydrogen peroxide being the most commonly used oxidant contained in said agents. These oxidative hair-treatment agents play an important role in a number of cosmetic hair treatments. In blonding, for example, the hair pigments are oxidatively broken down by the action of oxidant-containing formulations which results in a brightening of the hair.

2. Description of Related Art

As a rule, blonding agents consist of two components, a hydrogen peroxide-containing formulation and a basic component. peroxodisulfates can be used to achieve a more pronounced effect. Because aqueous hydrogen peroxide solutions are very difficult to apply to the hair in a controlled manner, more or less thickened oxidizing emulsions are used. The consistency-imparting agent for such emulsions is in most cases a long-chain fatty alcohol, the emulsifiers most frequently being fatty alcohol ethoxylates, alkylsulfates, alkyl ether sulfates etc. Although these white formulations can be well localized on the hair, the ability of the hairdresser to see the condition of the hair through the formulation after said formulation has been applied to the hair is very limited. To have control of the brightening efficacy while the brightening formulation is acting on the hair, namely to be able to observe the degree of hair brightening through the applied formulation at any time, it would be desirable for the formulation to be transparent. At the same time, depending on the nature of the product, the formulation should be more or less thickened thus allowing controlled application to the hair, it should not run off the hair and thus it should come in contact with the skin only to a minor extent, which would enhance the product's acceptance and reduce the risk of skin irritations.

These properties (transparency and thickened consistency) would also be desirable for other hair treatments, for example for permanent hair deformation brought about by reducing agent-containing formulations. For lasting hair deformation, the hair is usually first treated with a deformation agent based on a keratin-reducing mercapto compound which opens the disulfide bridges of hair keratin, after which the hair is brought into the desired shape. As a rule, the deformation agent is a keratin-reducing mercapto compound, for example a salt or ester of a mercaptocarboxylic acid. The hair is then rinsed with water and oxidatively post-treated with a fixing agent. As a result, the previously opened disulfide bridges are reconnected in a new way.

In certain embodiments of the permanent hair deformation, the hair is first treated with a reducing cream, usually a thioglycolate-containing cream, and then brought into the desired shape by means of suitable auxiliary agents such as clips or a certain kind of rollers. After an exposure time which depends on the condition of the hair, the thioglycolate-based hair-deformation agent is rinsed out after which an oxidant-containing formulation is applied to the hair for fixing purposes. As a rule, the oxidant is hydrogen peroxide. The agents imparting consistency to these emulsions are in most cases long-chain fatty alcohols and the emulsifiers used cases most frequently are fatty alcohol ethoxylates, alkylsulfates and alkyl ether sulfates.

Here, too, the drawback of the emulsions is that they are not clear and transparent but white and turbid. After the formulation has been applied, therefore, the hairdresser can observe changes in the shape of the hair only to a very limited extent. To have optimum control over the hair shaping during the action of the fixing formulation on the hair, namely to be able to observe the shape of the hair through the applied formulation at any time, it would be desirable for the formulation to be transparent. At the same time, depending on the nature of the product, the formulation should here, too, be more or less thickened and be salt-resistant so that said formulation could be applied to the hair in controlled manner without it running off. It is particularly advantageous if the agent for oxidative treatment of the hair does not run off the roller at all so that the fixation can be carried out with the hair-dresser's customer sitting in the upright position and without the customary use of a washing pan during the treatment period.

Long-term thickening of oxidant-containing formulations with polymeric thickeners that form transparent gels has a destabilizing effect on the oxidant used. From a technical point of view, this necessarily leads either to poor results because of the reduced oxidant content or to dangerous deformations including destruction of the container holding these agents (known as swelling). When the most frequently employed oxidant, namely hydrogen peroxide, is used, it has thus far been necessary to adjust the pH to 2 to 3 to stabilize the hydrogen peroxide. This leads to another problem: At such a low pH, no suitable thickening polymers are thus far known that would impart to the agent sufficient viscosity and at the same time give a transparent formulation which over a period of 6 months at 40° C. would show a stable viscosity, be peroxide-resistant and have a stable pH.

BRIEF SUMMARY OF THE INVENTION

The goal was therefore to provide an agent for carrying out oxidative treatment, particularly of hair, that would not show the afore-indicated drawbacks, namely that would have a gel-like consistency, would be transparent at the same time, would not drip off the hair and over a period of 6 months at 40° C. would show a constant viscosity, a constant pH and a constant peroxide content.

This goal cannot be reached by selecting a method known to those skilled in the art and consisting of simply thickening an aqueous hydrogen peroxide solution with a thickener that appears to be suitable. Such mixtures do not show the required long-term stability over 6 months at 40° C.

Surprisingly, we have now found that this goal can be reached in outstanding manner if the transparent, agent in gel form for the oxidative treatment contains at least one oxidant, at least one specific peroxide stabilizer, at least one specific polymer thickener and water or an aqueous solvent.

DETAILED DESCRIPTION OF THE INVENTION

Preferably, the agent is in the form of a gel and most preferably it is in the form of a gel and is transparent.

It is possible to use as the oxidant any oxidizing compound that has thus far been used for oxidative treatment of, for example, hair. Examples of such oxidizing compounds are hydrogen peroxide, alkali metal bromates, such as, for example, ammonium bromate, alkaline earth metal bromates, alkali metal persulfates, alkaline earth metal persulfates, ammonium persulfate, alkali metal perborates, alkaline earth metal perborates, ammonium perborate, alkali metal percarbonates, alkaline earth metal percarbonates, ammonium perborate [sic], calcium peroxide and sodium iodate. Preferably, different grades of hydrogen peroxide are used (for example the standard cosmetic grade and particularly a highly stabilized grade). The amount of oxidant present in the fixing agent varies depending on the duration of application and the use temperature. Usually, the oxidant is present in amount from 0.1 to 25 wt. %, preferably in an amount from 2 to 14 wt. % and most preferably in an amount from 4 to 12 wt. %.

The pH of the formulation, particularly when a peroxide is used, ranges from 2 to 6 and preferably from 3 to 5. When a bromate is used, the pH preferably ranges from 6 to 9 and most preferably from 7 to 8.5.

The agent of the invention also contains one or more stabilizers preferably selected from among the dialkali metal hydrogen phosphates, p-acetamidophenol, hydroxyquinoline salts, salicylic acid and the salts thereof, 1-hydroxyethane-1, 1-diphosphonic acid, tetrasodium 1-hydroxyethane-1,1-diphosphonate (CAS 3794-83-0; CTFA: TETRASODIUM ETIDRONATE), tetrasodium iminodisuccinate (CAS 144538-83-0; CTFA: TETRASODIUM IMINODISUCCINATE), ethylenediaminetetraacetic acid tetrasodium salt (INCI: EDTA) and N-(4-ethoxyphenyl)acetamide (CTFA: PHENACETIN).

Particularly suitable peroxide stabilizers are those listed in the following table.

| No. | CTFA/INCI Name | Chemical Designation |
|---|---|---|
| (1) | DISODIUM PHOSPHATE | disodium hydrogen phosphate |
| (2) | ACETAMINOPHEN | p-acetamidophenol |
| (3) | HYDROXYQUINOLINE SULFATE | 8-hydroxyquinoline sulfate |
| (4) | SALICYLIC ACID | salicylic acid and the salts thereof |
| (5) | EDITRONIC ACID | 1-hydroxyethane-1,1-diphosphonic acid and the tetrasodium salt thereof |
| (6) | TETRASODIUM IMINODISUCCINATE | tetrasodium iminodisuccinate |
| (7) | PHENACETIN | N-(4-ethoxyphenyl)acetamide |

The peroxide stabilizers, alone or in admixture with one another, are preferably contained in the agent of the invention at a concentration from 0.01 to 2 wt. % and most preferably in an amount from 0.05 to 0.3 wt. %.

Preferred are the following peroxide stabilizer combinations:
EDITRONIC ACID and SALICYLIC ACID
EDITRONIC ACID and DISODIUM PHOSPHATE
TETRASODIUM EDITRONATE and SALICYLIC ACID
TETRASODIUM EDITRONATE and SALICYLIC ACID
TETRASODIUM EDITRONATE and DISODIUM PHOSPHATE The agent of the invention most preferably contains the peroxide stabilizer combination in the following amounts:
0.1 wt. % of EDITRONIC ACID and 0.1 wt. % of SALICYLIC ACID
0.05 wt. % of EDITRONIC ACID and 0.15 wt. % of DISODIUM PHOSPHATE
0.05 wt. % of TETRASODIUM EDITRONATE and 0.15 wt. % of SALICYLIC ACID
0.15 wt. % of TETRASODIM EDITRONATE and 0.05 wt. % of SALICYLIC ACID
0.1 wt. % of TETRASODIUM EDITRONATE and 0.1 wt. % of DISODIUM PHOSPHATE When only one peroxide stabilizer is used, it is preferably selected from among TETRASODIUM EDITRONATE, salicylic acid and EDITRONIC ACID, the preferred use concentration in each case being 0.2 wt. %.

The preferred polymer thickeners are the following:

| No. | INCI/CTFA NAME | Chemical Designation |
|---|---|---|
| (8) | ACRYLATES COPOLYMER | Copolymer of acrylic acid and methacrylic acid or of simple esters thereof |
| (9) | ACRYLATES/C10–30 ALKYL ACRYLATE CROSSPOLYMER | Copolymer of $C_{10-30}$ alkyl acrylate and acrylic acid, methacrylic acid or simple esters thereof, crosslinked with an allyl ether of sucrose or an allyl ether of pentaerythritol |
| (10) | ACRYLATES/ACRYLAMIDE COPOLYMER | Copolymer of acrylamide and acrylic acid, methacrylic acid or a simple ester thereof (CAS No. 9003-06-9) |
| (11) | AMMONIUM ACRYLOYLDI-METHYLTAURATE/ BEHENETH-25 METHACRYLATE COPOLYMER | Copolymer of ammonium acryloyldimethyltaurate and Beheneth-25 methacrylate |
| (12) | AMMONIUM ACRYLOYLDI-METHYLTAURATE/VP COPOLYMER | Copolymer of ammonium acryloyldimethyltaurate and vinylpyrrolidone |
| (13) | CARBOMER | Homopolymer of acrylic acid, methacrylic acid, crosslinked with an allyl ether of sucrose, of pentaerythritol or of propylene |
| (14) | HYDROXYPROPYL STARCH PHOSPHATE | Hydroxypropyl ether of distarch phosphate |
| (15) | POLYQUATERNIUM-44 | Copolymer of 3-methyl-1-vinyl-1H-imidazolium methylsulfate and 1-vinyl-2-pyrrolidone |
| (16) | POLYQUATERNIUM-37 | N,N,N-Trimethyl-2-[(methyl-1-keto-2-propenyl)oxy] chloride homopolymer |
| (17) | POLYQUATERNIUM-37, MINERAL OIL, SORBITAN OLEATE, PEG-1/PPG-6 TRIDECCETH 6, C10–12 ALKANE/CYCLOALKANE | Mixture of N,N,N-trimethyl-2-[(methyl-1-keto-2-propenyl)oxy] chloride, homopolymer, sorbitan monooleate, polyethylene glycol/ polypropylene glycol tridecyl ether, $C_{10-12}$-alkanes and cycloalkanes (CAS 64742-48-9) |
| (18) | POLYQUATERNIUM-37, SORBITANE OLEATE, PROPYLENE GLYCOL DICAPRYLATE/DICAPRATE, | Mixture of N,N,N-trimethyl-2-[(methyl-1-keto-2-propenyl)oxy] chloride, homopolymer, |

-continued

| No. | INCI/CTFA NAME | Chemical Designation |
|---|---|---|
| | PPG-1 TRIDECETH-6, C10-12 ALKANE/ CYCLOALKANE | sorbitan monooleate, propylene glycol dicaprylate (EINECS 271-516-3), polypropylene glycol tridecyl ether, $C_{10-12}$ alkanes and cycloalkanes (CAS 64742-48-9) |
| (19) | SODIUM MAGNESIUM SILICATE | Sodium magnesium silicate |

The agent of the invention contains the polymer thickeners, alone or in admixture with one another, preferably in an amount from 0.1 to 5.0 weight percent, most preferably in an amount from 0.5 to 3.0 weight percent and optimally in an amount from 1.5 to 2.5 weight percent.

The agent of the invention also contains water or an aqueous solution. The water is preferably present in an amount from 50 to 98 wt. %, more preferably in an amount from 65 to 85 wt. % and most preferably in an amount from 65 to 80 wt. %.

The agent of the invention, for example one for oxidative treatment of hair, can contain cationic polymers, preferably in an amount from 0.1 to 2 weight percent, the following cationic polymers or mixtures of said cationic polymers being suitable: cationic cellulose derivatives, for example cationic cellulose ethers (for example CTFA: POLYQUATERNIUM-10), polydimethylaminoethyl methacrylate (75% quaternized with dimethyl sulfate or 100% with methyl chloride or methyl bromide), beta-methacryloxyethyltrimethylammonium methosulfate homopolymers (CTFA: POLYQUATERNIUM-14), beta-methacryloxy-ethyltrime-thylammonium methosulfate/acrylamide copolymers (CTFA: POLYQUATERNIUM-5), beta-methacryloxyethyltrimethylammonium methosulfate/vinylpyrrolidone copolymers (CTFA: POLYQUATERNIUM-11), N-vinylpyrrolidone/methacrylamidopropyltrimethylamammonium chloride copolymers and cationic chitosan derivatives.

Particularly preferred among these cationic polymers are the following: polydimethylaminoethyl methacrylate (75% quaternized with dimethyl sulfate), N-vinylpyrrolidone/methacrylamidopropyltrimethylammonium chloride copolymers, beta-methacryloxyethyltrimethylammonium methosulfate/vinylpyrrolidone copolymers and beta-methacryloxyethyl-trimethylammonium methosulfate homopolymers.

Moreover, the agent of the invention, particularly one for oxidative treatment of hair, can additionally contain nonionic surface-active compounds, for example fatty alcohol polyglycol ethers with a low degree of ethoxylation, for example ethoxylated alkylphenols with 1 to 5 ethylene oxide units in the molecule, or ethoxylated sorbitan fatty esters. The nonionic surface-active compounds are contained in the agent of the invention preferably in a total amount from 0.1 to 6 weight percent.

The agent of the invention can also contain amphoteric surface-active compounds, for example at a concentration of 0.1 to 3 weight percent, suitable being, for example, the following amphoteric surface-active compounds or mixtures of these amphoteric surface-active compounds: carboxyl derivatives of imidazole, for example CTFA: COCOAMPHODIPROPIONATE, CTFA: SODIUM COCOAMPHOACETATE or CTFA: COCOBETAINAMIDO AMPHOPROPIONATE (CAS 100085-64-1); N-alkylbetains and N-alkylamidobetains, N-alkylsulfobetains, N-alkylaminopropionates, alkyldimethylcarboxymethylammonium salts with 12 to 18 carbon atoms and fatty acid alkylamidobetains, for example fatty acid amidopropyldimethylaminoacetic acid betain.

The agent of the invention can of course also contain additives commonly used for such agents, for example dyes or alcohols, for example ethanol, propanol, isopropanol, ethylene glycol, 1,2-propylene glycol and 1,2,3-propanetriol (glycerol); dissolution promoters, buffering substances, perfume oils, defoamers and hair-conditioning or hair-care constituents, for example lanolin derivatives, cholesterol or betain. Moreover, the agent of the invention can contain additional additives, for example swelling and penetration agents, for example urea, 2-pyrrolidone, 1-methyl-2-pyrrolidone and dipropylene glycol monomethyl ether. The agent of the invention contains the additives in an amount from 0.1 to 50 wt. % and preferably from 1 to 20 wt. %. The amount of alcohols used is preferably from 5 to 15 wt. %.

The agent of the invention preferably has a viscosity from 100 to 30,000 mPa s, more preferably from 300 to 18,000 mPa s and most preferably from 300 to 5,000 mPa s measured at 25° C. The viscosity data were obtained with a Haake VT 550 Rotational Viscosimeter at a shearing rate of 12.9 per second. An NV- or MV-type double-slit cylindrical measuring device was used.

The agent of the invention for carrying out an oxidative treatment can be in the form of a uniform two-component preparation and in that case is prepared only just before use by mixing the pure polymer thickener or a composition containing the polymer thickener (Component 1) with an aqueous solution of the oxidant, preferably with an aqueous hydrogen peroxide solution (Component 2).

For decolorizing or blonding hair, too, oxidizing preparations are commonly used which are obtained by dissolving a blonding agent mixture (powdered mixture of alkali metal salts and inorganic persalts, for example sodium persulfate or ammonium persulfate) in an aqueous hydrogen peroxide solution.

Our goal was to provide a storage-stable agent for decolorizing or blonding human hair which would be prepared before use by simple shaking or stirring with a thickened, hydrogen peroxide-containing agent and which besides its absolutely dust-free appearance and application form would ensure maximum blonding efficacy and at the same time outstanding storage stability.

Before use, a blonding mixture that in and of itself is known is mixed with an aqueous hydrogen peroxide gel to form an applicable blonding agent, the mixing being carried out in a bowl or by shaking in an application bottle. The mixing ratio of blonding agent to oxidant when a 6-12% hydrogen peroxide gel of the invention is used amounts to 1:1 to 1:3.

The ready-to-use agent for decolorizing or blonding hair thus obtained is uniformly applied to the hair and after an exposure period of 15 to 60 min at room temperature (20-25° C.) or of 10 to 50 min with heating (30-50° C.) is rinsed out with water.

In a particular embodiment of the present invention, the agent of the invention for oxidative treatment can also be formulated as the oxidizing component of an oxidation hair colorant.

The ready-to-use oxidation colorant is prepared just before use by mixing a dye carrier composition with the agent of the invention for oxidative treatment.

In this case, too, suitable oxidants are mainly hydrogen peroxide or the products of addition thereof to urea, melamine or sodium bromate in a 1-12% and preferably 6% solution, hydrogen peroxide being particularly preferred.

To this end, the dye carrier composition and the agent of the invention for oxidative treatment are mixed with one another in a weight ratio of 5:1 to 1:3, a weight ratio of 1:1 to 1:2 being particularly preferred.

To adjust the pH of the dye carrier and of the agent of the invention for oxidative treatment, depending on the desired pH, a dilute organic or inorganic acid, for example phosphoric acid, ascorbic acid or lactic acid, or an alkaline substance, for example monoethanolamine, triethanolamine, 2-amino-2-methyl-lpropanol, ammonia, sodium hydroxide, potassium hydroxide or tris(hydroxymethyl)aminomethane, can be used.

After the dye carrier composition has been mixed with the agent for oxidative treatment, an amount of the resulting ready-to-use oxidation hair colorant sufficient for the hair treatment is applied to the hair. This amount depends on the hair fullness and generally ranges from about 60 to 200 g.

Preferably, the agent for oxidative treatment can be an agent for fixing the hair after a reductive permanent deformation treatment (permanent waving or hair smoothing).

The fixing agent is applied after the reductive deformation agent (for example a 10% ammonium thioglycolate solution with a pH of 8.5) has acted for a length of time sufficient to bring about a permanent hair deformation. Depending on the condition of the hair, on the pH, on the deformation efficacy of the agent and on the use temperature, the time of action of the reductive deformation agent is about 5 to 45 minutes (5 to 20 minutes with heating; 20 to 45 minutes without heating). The hair is then rinsed with water after which it is subjected to oxidative post-treatment with about 20 to 300 g and preferably with 60 to 150 g of the fixing agent of the invention (preferably as in Examples 15 to 27). After the fixing agent has acted for about 1 to 20 min and preferably for 6 to 10 min, the rollers are removed and the rolled hair, if necessary, is subjected to another oxidative post-treatment with the fixing agent for 1 to 5 minutes. The hair is then rinsed with water, arranged into a hairdo and dried.

The hair thus treated exhibits a uniform and durable deformation and is conditioned in an outstanding manner.

The advantages of the agent of the invention lie in an increase in viscosity, in an unproblematic application and particularly in the fact that the formulation exhibits clarity which allows visual control of the action on the hair, and in long-term storage stability of the formulations without undesirable peroxide degradation, undesirable viscosity fluctuations and undesirable changes in pH during storage.

The following examples will explain the subject matter of the invention in greater detail.

EXAMPLES

Example 1

| | |
|---|---|
| AMMONIUM ACRYLOYLDIMETHYLTAURATE/VP COPOLYMER (No. 12) | 2.00 g |
| Hydrogen peroxide | 10.00 g |
| EDITRONIC ACID (No. 5) | 2.05 g |
| Disodium hydrogen phosphate | 0.04 g |
| 1,2,3-Propanetriol | 12.00 g |
| Phosphoric acid | 0.14 g |
| Water | to 100.00 g |

The gel had a viscosity of 9,500 mPa s at 25° C. and a pH of 3.5

Example 2

| | |
|---|---|
| AMMONIUM ACRYLOYLDIMETHYLTAURATE/ BEHENETH-25 METHACRYLATE COPOLYMER (No. 11) | 2.00 g [sic] |
| Hydrogen peroxide | 12.00 g |
| Salicylic acid | 0.05 g |
| Disodium hydrogen phosphate | 0.15 g |
| Phosphoric acid | 0.13 g |
| Water, demineralized | to 100.00 g |

The gel had a viscosity of 15,000 mPa s at 25° C. and a pH of 4.0.

Example 3

| | |
|---|---|
| ACRYLATES/$C_{10-30}$ ALKYL ACRYLATE CROSSPOLYMER (No. 12) | 2.10 g |
| Hydrogen peroxide | 11.00 g |
| EDITRONIC ACID (No. 5) | 0.15 g |
| Disodium hydrogen phosphate | 0.05 g |
| 1,2,3-Propanetriol | 10.00 g |
| Sodium hydroxide | 0.09 g |
| Water, demineralized | to 100.00 g |

The gel had a viscosity of 9,500 mPa s at 25° C. and a pH of 3.5.

Example 4

| | |
|---|---|
| POLYQUATERNIUM-37 (No. 16) | 2.50 g |
| Hydrogen peroxide | 12.00 g |
| Salicylic acid | 0.10 g |
| ACETAMINOPHEN (No. 2) | 0.10 g |
| 1,2,3-Propanetriol | 10.00 g |
| Phosphoric acid | 0.12 g |
| Water, demineralized | to 100.00 g |

The gel had a viscosity of 7,500 mPa s at 25° C. and a pH of 3.5.

Example 5

| | |
|---|---|
| POLYQUATERNIUM 37, MINERAL OIL, SORBITAN OLEATE, PPG-1/PPG-6 TRIDECCETH 6, $C_{10-12}$ ALKANE/ CYCLOALKANE (No. 17) [sic] | 2.50 g |
| Hydrogen peroxide | 12.00 g |
| Salicylic acid | 0.15 g |
| HYDROXYQUINOLINE SULFATE (No. 3) | 0.05 g |
| 1,2,3-Propanetriol | 15.00 g |
| Phosphoric acid | 0.09 g |
| Water, demineralized | to 100.00 g |

The gel had a viscosity of 6,800 mPa s at 25° C. and a pH of 3.5.

Example 6

| | |
|---|---|
| AMMONIUM ACRYLOYLDIMETHYLTAURATE/ BEHENETH-25 METHACRYLATE COPOLYMER (No. 11) | 2.00 g |
| Hydrogen peroxide | 9.00 g |
| Salicylic acid | 0.10 g |
| ACETAMINOPHEN (No. 2) | 0.10 g |
| 1,2,3-Propanetriol | 10.00 g |
| Phosphoric acid | 0.17 g |
| Water, demineralized | to 100.00 g |

The gel had a viscosity of 23,500 mPa s at 25° C. and a pH of 4.0.

Example 7

| | |
|---|---|
| AMMONIUM ACRYLOYLDIMETHYLTAURATE/ BEHENETH-25 METHACRYLATE COPOLYMER (No. 11) | 1.00 g |
| AMMONIUM ACRYLOYLDIMETHYLTAURATE/VP COPOLYMER (No. 12) | 1.00 g |
| Hydrogen peroxide | 10.00 g |
| Salicylic acid | 0.05 g |
| Disodium hydrogen phosphate | 0.15 g |
| 1,2,3-Propanetriol | 10.00 g |
| Phosphoric acid | 0.11 g |
| Water, demineralized | to 100.00 g |

The gel had a viscosity of 16,000 mPa s at 25° C. and a pH of 3.5.

Example 8

| | |
|---|---|
| ACRYLATES/C10-30 ALKYL ACRYLATE CROSSPOLYMER (No. 9) | 1.00 g |
| AMMONIUM ACRYLOYLDIMETHYLTAURATE/ BEHENETH-25 METHACRYLATE COPOLYMER (No. 11) | 1.00 g |
| Hydrogen peroxide | 10.00 g |
| Salicylic acid | 0.05 g |
| Disodium hydrogen phosphate | 0.15 g |
| Castor oil ethoxylated with 35 ethylene oxide groups | 0.50 g |
| Hydrogenated castor oil ethoxylated with 40 ethylene oxide groups | 1.00 g |
| Perfume oil | 0.15 g |
| 1,2-Propylene glycol | 2.00 g |
| Ethanol | 2.00 g |
| Phosphoric acid | 0.11 g |
| Water, demineralized | to 100.00 g |

The gel had a viscosity of 19,500 mPa s at 25° C. and a pH of 3.5.

Example 9

| | |
|---|---|
| ACRYLATES/C10-30 ALKYL ACRYLATE CROSSPOLYMER (No. 9) | 2.00 g |
| Hydrogen peroxide | 10.00 g |
| Salicylic acid | 0.05 g |
| Disodium hydrogen phosphate | 0.15 g |
| 1,2,3-Propanetriol | 10.00 g |
| Castor oil ethoxylated with 35 ethylene oxide groups | 0.50 g |
| Hydrogenated castor oil ethoxylated with 40 ethylene oxide groups | 1.90 g |
| Perfume oil | 0.15 g |
| 1,2-Propylene glycol | 2.00 g |
| Urea | 2.00 g |
| Isopropanol | 2.00 g |
| Phosphoric acid | 0.15 g |
| Water, demineralized | to 100.00 g |

The gel had a viscosity of 13,000 mPa s at 25° C. and a pH of 4.0.

Example 10

Component 1

AMMONIUM ACRYLOYLDIMETHYLTAURATE/BEHENETH-25 METHA—2.00 g CRYLATE COPOLYMER (No. 11)

| Component 2 | |
|---|---|
| Hydrogen peroxide | 9.00 g |
| Salicylic acid | 0.10 g |
| ACETAMINOPHEN (No. 2) | 0.10 g |
| 1,2,3-Propanetriol | 10.00 g |
| Phosphoric acid | 0.17 g |
| Water, demineralized | to 98.00 g |

Components 1 and 2 were mixed with one another just before use. The gel had a viscosity of 22,000 mPa s at 25° C. and a pH of 3.5.

Example 11

| Component 1 | |
|---|---|
| AMMONIUM ACRYLOYLDIMETHYLTAURATE/ BEHENETH-25 METHACRYLATE COPOLYMER (No. 11) | 2.00 g |
| 1,3-Bis(hydroxymethyl)-5,5-dimethylimidazolidin-2,4-dione (+) [sic] (CTFA: DMDM HYDANTOIN) | 0.30 g |
| Phosphoric acid | 0.20 g |
| Water, demineralized | 47.50 g |

| Component 2 | |
|---|---|
| Hydrogen peroxide | 9.00 g |
| Salicylic acid | 0.10 g |
| ACETAMINOPHEN (No. 2) | 0.10 g |
| 1,2,3-Propanetriol | 10.00 g |
| Phosphoric acid | 0.17 g |
| Water, demineralized | to 50.00 g |

Components 1 and 2 were mixed with one another just before use. The gel had a viscosity of 23,000 mPa s at 25° C. and a pH of 3.0.

Example 12

| | |
|---|---|
| AMMONIUM ACRYLOYLDIMETHYLTAURATE/ VP COPOLYMER (No. 12) | 2.00 g |
| Hydrogen peroxide | 6.00 g |
| EDITRONIC ACID (No. 5) | 2.05 g |
| Disodium hydrogen phosphate | 0.04 g |
| 1,2,3-Propanetriol | 12.00 g |
| Phosphoric acid | 0.14 g |
| Water | to 100.00 g |

The gel had a viscosity of 9,300 mPa s at 25° C. and a pH of 3.5.

Example 13

Blonding Agent

| Component 1 Blonding agent mixture | |
|---|---|
| Potassium persulfate | 25.00 g |
| Ammonium persulfate | 18.00 g |
| Sodium metasilicate | 23.00 g |
| Sodium alginate | 2.00 g |
| Xanthan gum | 2.00 g |
| Acrylic acid polymer (CTFA: Carbomer) | 0.50 g |
| Isopropyl palmitate | 26.50 g |
| Beeswax | 2.50 g |
| Ethylenediaminetetraacetic acid | 0.50 g |
| | 100.00 g |

In a bowl and by use of a brush, 25 g of the blonding agent mixture (Component 1) was mixed uniformly with 25 g of a hydrogen peroxide-containing gel (Component 2) having the following composition:

| Component 2 Hydrogen Peroxide Gel | |
|---|---|
| AMMONIUM ACRYLOYLDIMETHYLTAURATE/ BEHENETH-25 METHACRYLATE COPOLYMER (No. 11) | 2.00 g |
| Hydrogen peroxide | 9.00 g |
| Salicylic acid | 0.05 g |
| Disodium hydrogen phosphate | 0.15 g |
| 1,2,3-Propanetriol | 10.00 g |
| Phosphoric acid | 0.13 g |
| Water, demineralized | to 100.00 g |

The gel had a viscosity of 23,000 mPa s at 25° C. and a pH of 3.5.

The resulting blonding agent was applied uniformly to medium-brown hair and after an exposure time of 30 minutes at room temperature was rinsed out with warm water after which the hair was dried. The hair treated in this manner was brightened to a bright-blond shade.

Example 14

Oxidation Hair Colorant

| Component 1 Dye Carrier Composition | |
|---|---|
| Ethanol | 8.00 g |
| Sodium lauryl ether sulfate, 28% aqueous solution | 10.00 g |
| Ammonia, 25% aqueous solution | 9.00 g |
| Ascorbic acid | 0.30 g |
| Sodium sulfite | 0.40 g |
| Oxidation dye mixture consisting of at least one coupler and at least one developer | 5 mmol |
| Water | to 100.00 g |

Just before use, 20 g of the dye carrier composition (Component 1) and 20 g of the 6% hydrogen peroxide gel indicated hereinbelow (Component 2) were mixed with one another to obtain the ready-to-use oxidation hair colorant.

| Component 2 Hydrogen Peroxide Gel | |
|---|---|
| AMMONIUM ACRYLOYLDIMETHYLTAURATE/ VP COPOLYMER (No. 12) | 2.00 g |
| Hydrogen peroxide | 6.00 g |
| EDITRONIC ACID (No. 5) | 2.05 g |
| Disodium hydrogen phosphate | 0.04 g |
| 1,2,3-Propanetriol | 12.00 g |
| Phosphoric acid | 0.14 g |
| Water | to 100.00 g |

The gel had a viscosity of 10,300 mPa s at 25° C. and a pH of 3.5.

The ready-to-use oxidation hair colorant thus obtained was then applied to human hair. After an exposure time of 30 min at 40° C., the hair was washed with a shampoo, rinsed with water and dried.

Example 15

Fixing Agent

| | |
|---|---|
| AMMONIUM ACRYLOYLDIMETHYLTAURATE/ VP COPOLYMER (No. 12) | 0.60 g |
| Hydrogen peroxide, 50% aqueous solution | 5.00 g |
| Polyoxyethylene(20) sorbitan monopalmitate (CTFA: POLYSORBATE 40) | 1.00 g |
| Perfume | 0.30 g |
| EDITRONIC ACID (No. 5) | 0.80 g |
| Disodium hydrogen phosphate | 0.05 g |
| Salicylic acid | 0.15 g |
| 1,2,3-Propanetriol | 1.00 g |
| Sodium hydroxide | 0.06 g |
| Phosphoric acid | 0.04 g |
| Water | to 100.00 g |

The fixing agent had a pH of 3.5. The viscosity of the agent amounted to 450 mPa s at 25° C.

After reductive hair deformation, the hair was fixed as described on page 11, lines 21-30.

The hair treated in this manner showed a lasting and uniform deformation and was conditoned in outstanding manner.

Example 16

Fixing Agent

| | |
|---|---|
| AMMONIUM ACRYLOYLDIMETHYLTAURATE/ VP COPOLYMER (No. 12) | 0.80 g |
| Hydrogen peroxide | 5.00 g |
| Polyoxyethylene(20) sorbitan monopalmitate (CTFA: POLYSORBATE 40) | 1.00 g |
| Perfume | 0.30 g |
| EDITRONIC ACID (No. 5) | 0.10 g |
| Disodium hydrogen phosphate | 0.05 g |
| Salicylic acid | 0.05 g |
| 1,2,3-Propanetriol | 1.00 g |
| Sodium hydroxide | 0.14 g |
| Phosphoric acid | 0.04 g |
| Water | to 100.00 g |

The fixing agent had a viscosity of 700 mPa s at 25° C. and a pH of 4.0.

Example 17

| | |
|---|---|
| AMMONIUM ACRYLOYLDIMETHYLTAURATE/ VP COPOLYMER (No. 12) | 0.70 g |
| Hydrogen peroxide | 5.00 g |
| Polyoxyethylene(20) sorbitan monopalmitate (CTFA: POLYSORBATE 40) | 1.00 g |
| Perfume | 0.30 g |
| EDITRONIC ACID (No. 5) | 0.05 g |
| Disodium hydrogen phosphate | 0.05 g |
| Salicylic acid | 0.15 g |
| Panthenol | 0.25 g |
| Sodium hydroxide | 0.10 g |
| Phosphoric acid | 0.04 g |
| Water | to 100.00 g |

The fixing agent had a viscosity of 720 mPa s at 25° C. and a pH of 3.0.

Example 18

| | |
|---|---|
| AMMONIUM ACRYLOYLDIMETHYLTAURATE/ VP COPOLYMER (No. 12) | 0.70 g |
| Hydrogen peroxide | 5.00 g |
| Polyoxyethylene(20) sorbitan monopalmitate (CTFA: POLYSORBATE 40) | 1.00 g |
| Perfume | 0.30 g |
| EDITRONIC ACID (No. 5) | 0.15 g |
| Salicylic acid | 0.05 g |
| PEG/PPG-25/25 DIMETHICONE | 1.00 g |
| Sodium hydroxide | 0.10 g |
| Phosphoric acid | 0.04 g |
| Water | to 100.00 g |

The fixing agent had a viscosity of 680 mPa s at 25° C. and a pH of 3.5.

Example 19

| | |
|---|---|
| POLYQUATERNIUM 37 (No. 16) | 0.80 g |
| Hydrogen peroxide | 5.00 g |
| Polyoxyethylene(20) sorbitan monopalmitate (CTFA: POLYSORBATE 40) | 1.00 g |
| Perfume | 0.30 g |
| EDITRONIC ACID (No. 5) | 0.15 g |
| Salicylic acid | 0.05 g |
| 1,2,3-Propanetriol | 3.00 g |
| Sodium hydroxide | 0.14 g |
| Phosphoric acid | 0.04 g |
| Water | to 100.00 g |

The fixing agent had a viscosity of 700 mPa s at 25° C. and a pH of 3.5.

Example 20

| | |
|---|---|
| POLYQUATERNIUM 37 (No. 16) | 0.80 g |
| Hydrogen peroxide | 5.00 g |
| Polyoxyethylene(20) sorbitan monopalmitate (CTFA: POLYSORBATE 40) | 1.00 g |
| Perfume | 0.30 g |
| EDITRONIC ACID (No. 5) | 0.15 g |
| Salicylic acid | 0.05 g |
| Cetyltrimethylammonium chloride | 0.15 g |
| Sodium hydroxide | 0.14 g |
| Phosphoric acid | 0.04 g |
| Water | to 100 g |

The fixing agent had a viscosity of 730 mPa s at 25° C. and a pH of 3.5.

Example 21

| | |
|---|---|
| AMMONIUM ACRYLOYLDIMETHYLTAURATE/ BEHENETH-25 METHACRYLATE COPOLYMER (No. 11) | 0.60 g |
| Hydrogen peroxide | 5.00 g |
| Polyoxyethylene(20) sorbitan monopalmitate (CTFA: POLYSORBATE 40) | 1.00 g |
| Perfume | 0.30 g |
| EDITRONIC ACID (No. 5) | 0.70 g |
| Disodium hydrogen phosphate | 0.05 g |
| Salicylic acid | 0.15 g |
| 1,2,3-Propanetriol | 1.00 g |
| Sodium hydroxide | 0.06 g |
| Phosphoric acid | 0.04 g |
| Water | to 100.00 g |

The fixing agent had a viscosity of 500 mPa s at 25° C. and a pH of 3.0.

Example 22

| | |
|---|---|
| AMMONIUM ACRYLOYLDIMETHYLTAURATE/ BEHENETH-25 METHACRYLATE COPOLYMER (No. 11) | 0.70 g |
| Hydrogen peroxide | 5.00 g |
| Polyoxyethylene(20) sorbitan monopalmitate (CTFA: POLYSORBATE 40) | 1.00 g |
| Perfume | 0.30 g |
| EDITRONIC ACID (No. 5) | 0.20 g |
| Disodium hydrogen phosphate | 0.05 g |
| Salicylic acid | 0.05 g |

-continued

| | |
|---|---|
| 1,2,3-Propanetriol | 1.00 g |
| Sodium hydroxide | 0.14 g |
| Phosphoric acid | 0.04 g |
| Water | to 100.00 g |

The fixing agent had a viscosity of 750 mPa s at 25° C.

Example 23

| | |
|---|---|
| AMMONIUM ACRYLOYLDIMETHYLTAURATE/ BEHENETH-25 METHACRYLATE COPOLYMER (No. 11) | 0.80 g |
| Hydrogen peroxide | 5.00 g |
| Polyoxyethylene(20) sorbitan monopalmitate (CTFA: POLYSORBATE 40) | 1.00 g |
| Perfume | 0.30 g |
| EDITRONIC ACID (No. 5) | 0.05 g |
| Disodium hydrogen phosphate | 0.05 g |
| Salicylic acid | 0.15 g |
| Panthenol | 0.25 g |
| Sodium hydroxide | 0.10 g |
| Phosphoric acid | 0.04 g |
| Water | to 100.00 g |

The fixing agent had a viscosity of 800 mPa s at 25° C. and a pH of 3.5.

Example 24

| | |
|---|---|
| ACRYLATES/C 10-30 ALKYL ACRYLATE CROSSPOLYMER (No. 9) | 0.65 g |
| Hydrogen peroxide | 5.00 g |
| Salicylic acid | 0.05 g |
| Disodium hydrogen phosphate | 0.15 g |
| Polyoxyethylene(20) sorbitan monopalmitate (CTFA: POLYSORBATE 40) | 1.00 g |
| Perfume oil | 0.15 g |
| 1,2,3-Propanetriol | 1.00 g |
| Ethoxylated castor oil with 35 ethylene oxide groups | 0.50 g |
| Ethoxylated hydrogenated castor oil with 40 ethylene oxide groups | 1.00 g |
| Panthenol | 0.21 g |
| Ethanol | 2.00 g |
| Sodium hydroxide | 0.12 g |
| Phosphoric acid | 0.04 g |
| Water, demineralized | to 100.00 g |

The fixing agent had a viscosity of 450 mPa s at 25° C. and a pH of 3.5.

Example 25

| | |
|---|---|
| ACRYLATES/C10-30 ALKYL ACRYLATE CROSSPOLYMER (No. 9) | 0.75 g |
| Hydrogen peroxide | 5.00 g |
| Polyoxyethylene(20) sorbitan monopalmitate (CTFA: POLYSORBATE 40) | 1.00 g |
| Perfume | 0.03 g |
| EDITRONIC ACID (No. 5) | 0.85 g |
| Disodium hydrogen phosphate | 0.50 g |
| Salicylic acid | 0.05 g |
| Ethoxylated hydrogenated castor oil with 60 ethylene oxide groups (CTFA: PEG-60 HYDROGENATED CASTOR OIL) | 1.00 g |
| Perfume oil | 0.30 g |
| 1,2-Propylene glycol | 2.00 g |
| Sodium hydroxide | 0.06 g |
| Phosphoric acid | 0.04 g |
| Water, demineralized | to 100.00 g |

The fixing agent had a viscosity of 600 mPa s at 25° C. and a pH of 3.5.

Example 26

| | |
|---|---|
| AMMONIUM ACRYLOYLDIMETHYLTAURATE/ BEHENETH-25 METHACRYLATE COPOLYMER (No. 11) | 0.30 g |
| AMMONIUM ACRYLOYLDIMETHYLTAURATE/ VP COPOLYMER (No. 12) | 0.32 g |
| Hydrogen peroxide | 5.00 g |
| EDITRONIC ACID (No. 5) | 0.85 g |
| Salicylic acid | 0.05 g |
| Ethoxylated hydrogenated castor oil with 60 ethylene oxide groups (CTFA: PEG-60 HYDROGENATED CASTOR OIL) | 1.00 g |
| Perfume oil | 0.30 g |
| Sodium hydroxide | 0.06 g |
| Phosphoric acid | 0.07 g |
| Water, demineralized | to 100.00 g |

The fixing agent had a viscosity of 600 mPa s at 25° C. and a pH of 3.5.

Example 27

| | |
|---|---|
| AMMONIUM ACRYLOYLDIMETHYLTAURATE/ BEHENETH-25 METHACRYLATE COPOLYMER (No. 11) | 0.32 g |
| ACRYLATES/C10-30 ALKYL ACRYLATE CROSSPOLYMER (No. 9) | 0.32 g |
| Hydrogen peroxide | 5.00 g |
| EDITRONIC ACID (No. 5) | 0.85 g |
| Salicylic acid | 0.05 g |
| Ethoxylated hydrogenated castor oil with 60 ethylene oxide groups (CTFA: PEG-60 HYDROGENATED CASTOR OIL) | 1.00 g |
| Perfume oil | 0.30 g |
| Sodium hydroxide | 0.06 g |
| Phosphoric acid | 0.06 g |
| Water, demineralized | to 100.00 g |

The fixing agent had a viscosity of 750 mPa s at 25° C. and a pH of 4.0.

The invention claimed is:

1. An agent for oxidative treatment consisting of:
   a) at least one oxidant,
   b) at least one peroxide stabilizer;
   c) at least one polymer thickener selected from the group consisting of
      (i) copolymers of acrylic acid,
      (ii) polymers with propyleneoxy groups,
      (iii) copolymers of vinylpyrrolidone, (iv) hydroxyalkylstarch phosphates, and
(v) alkali metal magnesium silicates
d) water or an aqueous solvent; and
e) optionally one or more of a nonionic surface-active compound, an amphoteric surface-active compound, a cationic polymer, a dye, an alcohol, a dissolution promoter, a buffering substance, a perfume oil, a defoamer, a lanolin derivative, cholesterol, betain, a swelling agent a penetration agent, a blonding agent, and a dilute organic or inorganic acid or base;
wherein the agent is transparent.

2. The agent as defined in claim 1 wherein the agent is in the form of a gel.

3. The agent as defined in claim 1, wherein the oxidant is selected from the group consisting of hydrogen peroxide, alkali metal bromates, alkaline earth metal bromates, ammonium bromate, alkali metal persulfates, alkaline earth metal persulfates, ammonium persulfate, alkali metal perborates, alkaline earth metal perborates, ammonium perborate, alkali metal percarbonates, alkaline earth metal percarbonates, calcium peroxide and sodium iodate.

4. The agent as defined in claim 1, wherein the agent contains a bromate as the oxidant and has a pH between 7 and 8.5.

5. The agent as defined in claim 1, wherein the agent has a pH of 2 to 6.

6. The agent as defined in claim 1, wherein the agent contains the oxidant in an amount from 0.1 to 25 weight percent.

7. The agent as defined in claim 1, wherein the peroxide stabilizer is selected from the group consisting of dialkali metal hydrogen phosphates, p-acetamidophenol, hydroxyquinoline salts, salicylic acid and salts thereof, 1-hydroxyethane-1,1-diphosphonic acid, tetrasodium 1-hydroxyethane-1,1-diphosphonate, tetrasodium iminodisuccinate, ethylene-diaminetetraacetic acid tetrasodium salt and N-(4-ethoxyphenyl)acetamide.

8. The agent as defined in claim 1, wherein the agent contains the stabilizer in an amount from 0.01 to 2 weight percent.

9. The agent a s defined in claim 1, wherein the stabilizer is a 2-component combination, the combination being selected from the following group consisting of:
EDITRONIC ACID and SALICYLIC ACID,
EDITRONIC ACID and DISODIUM PHOSPHATE,
TETRASODIUM EDITRONATE and SALICYLIC ACID,
TETRASODIUM EDITRONATE and SALICYLIC ACID, and
TETRASODIUM EDITRONATE and DISODIUM PHOSPHATE.

10. The agent as defined in claim 1, wherein the stabilizer is present in an amount of from 0.1 to 0.3 wt % and the stabilizer is selected from the group consisting of TETRASODIUM EDITRONATE, SALICYLIC ACID and EDITRONIC ACID.

11. The agent as defined in claim 1, wherein the polymer thickener is selected from the group consisting of: ACRYLATES COPOLYMER;
ACRYLATES/C10-30 ALKYL ACRYLATE CROSSPOLYMER;
ACRYLATES/ACRYLAMIDE COPOLYMER; AMMONIUM ACRYLOYLDIMETHYLTAURATE/BEHENETH-25 METHACRYLATE COPOLYMER;
AMMONIUM ACRYLOYLDIMETHYLTAURATE/VP COPOLYMER; CARBOMER;
HYDROXYPROPYL STARCH PHOSPHATE; POLYQUATERNIUM-44;
POLYQUATERNIUM-37; POLYQUATERNIUM-37, MINERAL OIL, SORBITAN OLEATE,
PEG-1/PPG-6 TRIDECCETH 6, C10-12 ALKANE/CYCLOALKANE; POLYQUATERNIUM-37, SORBITANE OLEATE, PROPYLENE GLYCOL DICAPRYLATE/DICAPRATE, PPG-1 TRIDECETH-6, C10-12 ALKANE/CYCLOALKANE; and SODIUM MAGNESIUM SILICATE.

12. The agent as defined in claim 1, wherein the agent contains the polymer thickener in art amount from 0.1 to 5.0 weight percent.

13. The agent as defined in claim 1, wherein the agent contains water in an amount from 50 to 98 wt.%.

14. The agent as defined in claim 1, wherein the agent contains an alcohol in an amount from 1 to 20 wt.%.

15. The agent as defined in claim 14, wherein the alcohol is 1,2,3-propanetriol.

16. The agent as defined in 1, wherein the agent contains at least one cationic polymer.

17. The agent as defined in claim 1, wherein the agent contains at least one amphoteric surface-active compound selected from the group consisting of the carboxyl derivatives of imidazole, N-alkylamidobetains, N-alkylsulfobetains N-alkylaminopropionates, alkyldimethyl-carboxymethylammonium salts with 12 to 18 carbon atoms and fatty acid alkylamidobetains.

18. The agent as defined in claim 1, wherein the agent has a viscosity of 100 to 30,000 mPa s measured at 25° C. with a VT 550 Haake Rotational Viscometer at a shearing rate of 12.9 per second.

19. The agent as defined in claim 1, wherein the agent is in the form of a 2-component preparation and is prepared just before use by mixing the pure polymer thickener or a composition containing the polymer thickener (Component 1) with an aqueous hydrogen peroxide solution (Component 2).

* * * * *